United States Patent [19]
Belliotti et al.

[11] Patent Number: 5,284,949
[45] Date of Patent: Feb. 8, 1994

[54] 2-SUBSTITUTED AMINO-4,6-DI-TERTIARY-BUTYL-5-HYDROXY-1,3-PYRIMIDINES AS ANTIINFLAMMATORY AGENTS

[75] Inventors: Thomas R. Belliotti, Ypsilanti; David T. Connor, Ann Arbor; Catherine R. Kostlan, Saline, all of Mich.

[73] Assignee: Warner-Lambert Company, Morris Plains, N.J.

[21] Appl. No.: 29,076

[22] Filed: Mar. 10, 1993

Related U.S. Application Data

[62] Division of Ser. No. 977,313, Nov. 16, 1992, Pat. No. 5,220,025, which is a division of Ser. No. 840,360, Feb. 24, 1992, Pat. No. 5,196,431.

[51] Int. Cl.$^5$ ............... C07D 239/02; A61K 31/505
[52] U.S. Cl. .................................................. 544/298
[58] Field of Search ........................................ 544/298

[56] References Cited

U.S. PATENT DOCUMENTS

| | | | |
|---|---|---|---|
| 4,711,888 | 12/1987 | Walker et al. | 514/269 |
| 4,859,679 | 8/1989 | Santini | 514/273 |
| 4,940,712 | 7/1990 | Walker et al. | 514/272 |

FOREIGN PATENT DOCUMENTS

| | | |
|---|---|---|
| 0164204 | 12/1985 | European Pat. Off. . |
| 0233461 | 8/1987 | European Pat. Off. . |
| 0319170 | 6/1989 | European Pat. Off. . |
| 2045756 | 11/1980 | United Kingdom . |

OTHER PUBLICATIONS

Lamattina et al, Tetrahedron Letters, vol. 25, No. 28, pp. 2957-2960 (1984).
Biochem., 1951, 48, pp. 400-406, Bray, et al.

*Primary Examiner*—Cecilia Tsang
*Attorney, Agent, or Firm*—Ronald A. Daignault; Elizabeth M. Anderson

[57] ABSTRACT

The present invention is novel compounds which are 2-substituted amino-4,6-di-tertiarybutyl-5-hydroxy-1,3-pyrimidines and pharmaceutically acceptable acid addition or base salts thereof, pharmaceutical compositions and methods of use therefor. The invention compounds are described as having activity as inhibitors of 5-lipoxygenase and/or cyclooxygenase providing treatment of conditions advantageously affected by such inhibition including inflammation, arthritis, pain, fever and the like. Thus, the present invention is also a pharmaceutical composition or method of manufacturing a pharmaceutical composition for the use of treating the noted conditions.

1 Claim, No Drawings

2-SUBSTITUTED AMINO-4,6-DI-TERTIARY-BUTYL-5-HYDROXY-1,3-PYRIMIDINES AS ANTIINFLAMMATORY AGENTS

This is a divisional of U.S. application Ser. No. 977,313 filed Nov. 16, 1992, now U.S. Pat. No. 5,220,025, which is a divisional of U.S. application Ser. No. 840,360 filed Feb. 24, 1992, now U.S. Pat. No. 5,196,431.

BACKGROUND OF THE INVENTION

The present invention is novel compounds which are 2-substituted amino-4,6-di-tertiary-butyl-5-hydroxy-1,3-pyrimidines and pharmaceutically acceptable acid addition or base salts thereof, pharmaceutical compositions and methods of use therefor. The invention compounds have activity as inhibitors of 5-lipoxygenase and/or cyclooxygenase providing treatment of conditions advantageously affected by such inhibition including, for example, rheumatoid arthritis, osteoarthritis, other inflammatory conditions, pain, fever, psoriasis, allergic diseases, asthma, inflammatory bowel disease, GI ulcers, cardiovascular conditions including ischemic heart disease and atherosclerosis, and ischemia-induced cell damage, particularly brain damage caused by stroke. They can also be used topically for treating acne, sunburn, psoriasis, and eczema. Also included are leukotriene mediated pulmonary, gastrointestinal, inflammatory, dermatological, and cardiovascular conditions. The disclosed compounds also have potential utility as antioxidants. However, overall the preferable use is to treat inflammatory conditions. Thus, the present invention is also a pharmaceutical composition or method of manufacturing a pharmaceutical composition for the use of treating the noted conditions.

2-Substituted-4,6-di-tertiary-butyl-5-hydroxy-1,3-pyrimidines are known to provide activity as inhibitors of 5-lipoxygenase and/or cyclooxygenase as described in co-pending U.S. application Ser. No. PCT/US 92/00443 of Jan. 17, 1992. The compounds described have no amino substituent at the 2-position of the pyrimidine moiety.

Numerous references disclose 2-amino-5-hydroxy pyrimidines. Such disclosed pyrimidines may also be substituted at the 4- and/or 6-positions with various groups including alkyls. For example, U.K. Patent Application Number 2045736 and the *Bioch. J.* 1951, 48, P. 400 shows the simple 2-amino-5-hydroxy-4,6-dimethyl-pyrimidine. Other substituted 2-aminopyrimidines are shown in U.S. Pat. No. 4711888, European Publication Numbers 319170, 233416, 1642 and U.S. Pat. Nos. 4,859,679 and 4,940,712.

In summary, the above references do not show the present 2-amino substituent in combination with a 5-hydroxy group and 4 and 6 ditertiarybutyl on a pyrimidine nucleus.

SUMMARY OF THE INVENTION

The present invention is a compound of the formula I

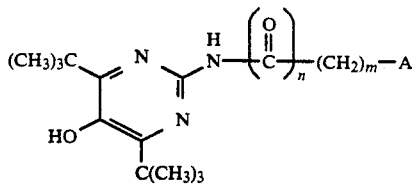

or pharmaceutically acceptable salts and hydrates thereof; wherein n is zero or one; m is an integer from zero to five, and A is a 5- or 6-membered heteroaromatic ring 1) which ring contains 1, 2 or 3 heteroatoms selected from S, O, or N wherein the heteroaromatic ring may not have more than one of O or S, 2) which ring is attached at a carbon in the ring,, and 3) which ring is optionally substituted by lower alkyl or COOR wherein R is hydrogen or lower alkyl. The lower alkyl or COOR is attached at one or more of the ring carbons. The present invention is also a compound of the formula

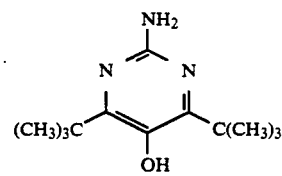

The above compound is an intermediate useful in the preparation of the compounds of formula I defined herein.

The present invention is further the use of an aminooxazole of the formula

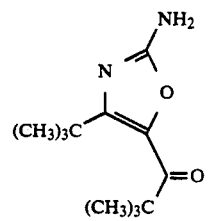

to prepare a compound of the formula

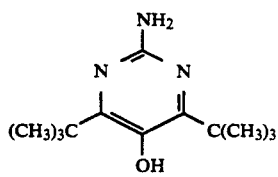

by reacting the aminooxazole with ammonium hydroxide at about 130° C. to about 190° in a closed vessel.

The present invention is also a pharmaceutical composition for the treatment of conditions advantageously affected by the inhibition of 5-lipoxygenase alone or together with the inhibition of cyclooxygenase, preferably the inhibition of both 5-lipoxygenase and cyclooxygenase which comprises an amount effective for the treatment of the condition of a compound of the formula I and the pharmaceutically acceptable acid addition or base salt thereof together with a pharmaceutically acceptable carrier. The condition is meant to include, for example, rheumatoid arthritis, osteoarthritis, other inflammatory conditions, pain, fever, psoriasis, allergic diseases, asthma, inflammatory bowel disease, GI ulcers, cardiovascular conditions including ischemic heart disease and atherosclerosis, and ischemia-induced cell damage particularly brain damage caused by stroke. They can also be used topically for treating acne, sunburn, psoriasis, and eczema. Also included are leukotriene mediated pulmonary, gastrointestinal, inflammatory, dermatological, and cardiovascular conditions. The disclosed compounds also have potential utility as antioxidants. However, overall the preferable use is to treat inflammatory conditions.

The present invention is also a method for treatment of the condition as noted above in a mammal, including humans, suffering therefrom with a compound of the formula I or the pharmaceutically acceptable acid addition or base salt thereof, in unit dosage form. The invention also provides for use of any such compound of formula I or salt thereof in the manufacture of a medical therapeutic agent.

Pharmaceutical composition or use of the compound or salt of formula I is meant to include treatment understood to be prophylactic pertinent to the foregoing named condition.

DETAILED DESCRIPTION OF THE INVENTION

"Heteroaromatic ring" means pyridinyl, pyrimidinyl, pyrrolyl, pyrazinyl, triazinyl, oxazolyl, isoxazolyl, pyrazolyl, pyridazinyl, imidazolyl, thiazolyl, isothiazolyl, thiadiazolyl, oxadiazolyl, triazolyl, and the like. These ring systems are meant to include rings having a lower alkyl or COOR, wherein R is hydrogen or lower alkyl, substituted on one or more of the ring carbons, and also includes all possible regioisomers. Such regioisomers are limited by a required attachment to the aminopyrimidinyl group through a carbon of the ring.

In the compounds of formula I the term "lower alkyl" includes an alkyl group of from one to six carbons such as methyl, ethyl, propyl, butyl, and the like and branched isomers thereof.

The compounds I of the invention may exist as tautomers which are readily determined from art recognized tautomerism.

Appropriate compounds of formula I are useful in the free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as methanesulfonic acid, ethanesulfonic acid, benzenesulfonic acid, p-toluenesulfonic acid, and the like, giving the hydrochloride, sulfamate, methanesulfonate, ethanesulfonate, benzenesulfonate, p-toluenesulfonate and the like, respectively, or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di- or triethanolamine; amino acids such as arginine and lysine; guanidine; choline N-methylglucosamine; M-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.,* "(1):1–19 (1977).) Salts of inorganic bases include sodium, potassium, calcium or the like.

The acid addition salts of said basic compounds are prepared either by dissolving the free base or acid of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric isomers. Thus, the invention includes the individual isomers and mixtures thereof. The individual isomers may be prepared or isolated by methods known in the art.

The compounds of the present invention are also meant to include hydrated or solvated forms, if possible.

Preferred compounds of the present invention are the compounds of formula I where n is zero or one and A is pyridyl or thiazolyl optionally substituted by lower alkyl or COOR. More preferred are the compounds of formula I wherein n is zero and A is thiazolyl optionally substituted by lower alkyl or COOR.

Particularly valuable are:
2-amino-4,6-bis(1,1-dimethylethyl)-5-hydroxypyrimidine,
4,6-bis(1,1-dimethylethyl)-5-hydroxy-2-(3-pyridylamido)pyrimidine,
4,6-bis(1,1-dimethylethyl)-2-[(4-methyl-2-thiazolyl)amino]-5-pyrimidinol,
2-([4,6-bis(1,1-dimethylethyl)-5-hydroxy-2-pyrimidinyl]amino)-4-thiazole-4-carboxylic acid ethyl ester, and
2-([4,6-bis(1,1-dimethylethyl)-5-hydroxy-2-pyrimidinyl]amino)-4-thiazolecarboxylic acid.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of formula I or pharmacologically acceptable salt thereof to achieve a therapeutic effect will, of course, vary both with the particular compound, the route of administration, the mammal under treatment, and the particular disorder or disease concerned. A suitable dose of a compound of formula I or pharmacologically acceptable salt thereof for a mammal suffering from, or likely to suffer from any condition as described hereinbefore is 0.1 μg–500 mg of the compound per kilograin body weight. In the case of systemic administration, the dose may be in the range of 0.5 to 500 mg of the compound per kilograin body weight, the most preferred dosage being 0.5 to 50 mg/kg of mammal body weight administered two or three times daily. In the case of topical administration, e.g., to the skin or eye, a suitable dose may be in the range 0.1 μg–100 Kg of the compound per kilogram, typically about 0.1 μg/kg.

In the case of oral dosing for the treatment or prophylaxis of arthritis or inflammation in general, due to any course, a suitable dose of a compound of formula I or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula I or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well-known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC Whole Cell 5-Lipoxygenase and Cyclooxygenase Assays

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; $Na_2HPO_4$, 1.15 g; $KH_2PO_4$, 0.2 g; and KCl, 0.2 g/l). Cells are finally suspended in PBS containing 1.0 mM calcium at a density of $2 \times 10^6$ cells/mL. Cells are incubated with and without test agent (in DMSO) (1% DMSO is without effect on arachidonic acid metabolism) for ten minutes at room temperature. Calcium ionophore A23187 (5 μM) is added and cells are incubated for 7 minutes at 37° C. The reaction is stopped by chilling the tubes on ice for 10 minutes. Cells are separated by centrifugation and the supernatant is stored at −20°. Aliquots (100 KL) are analyzed for $LTB_4$ and $PGF_{2\alpha}$ using radioimmunoassay kits as provided by the supplier.

Carrageenan-Induced Rat Foot Paw Edema-2 (CFE-2) Assay: Protocol

Carrageenan solution (1% w/v) is prepared by dissolving 100 mg carrageenan (marine Colloidal Div., Springfield, N.J.) in 10 mL of sterile saline (0.9%) solution (Travenol). The solution is vortexed for 30 to 45 minutes. Animals are dosed with compound one hour before carrageenan challenge. Foot paw edema is induced by injecting 0.10 mL of the 1% carrageenan subcutaneously into the plantar portion of the right hind paw of each rat under light anesthesia. Initial foot paw volume is measured immediately following carrageenan challenge using mercury plethysmography (Buxco Electronics). Edema is measured 5 hours after carrageenan. The difference between the 5-hour and the initial paw volume is expressed as delta edema. The delta edema for each test group of animals is used to calculate the percent inhibition of edema achieved by the compound at the test dose compared with the vehicle control group. The $ID_{40}$ (the dose at which swelling is inhibited by 40%) is calculated by probit analysis for the dose at which 40 percent inhibition occurs.

Mycobacterium-Induced Rat Footpad Edema Assay (MFE): Protocol

*Mycobacterium butyricum* (5 mg/ml) is suspended in paraffin oil by sonication for ten minutes in an ice bath. Footpad edema is induced on Day 0 by injecting 0.1 mL of the Mycobacterium mixture into the left hindpaw of lightly anesthetized rats. Swelling in the injected hindpaw is determined by mercury plethysmography 72 hours after injection. Groups of rats are treated with test compounds (suspended in 0.5% hydroxypropyl methylcellulose with 0.2% Tween-80) or vehicle 1 hour before Mycobacterium injection and on Days 1 and 2. Inhibition of swelling is determined by comparing the change in hindpaw volume in compound- and vehicle-treated rats. An $ID_{40}$ (the dose at which swelling is inhibited by 40%) is calculated by probit analysis.

Gastric Ulcerogenicity (UD): Protocol

Male outbred Wistar rats (100–250 g) are fasted for 24 hours. After fasting, test compounds are administered orally (in 2 ml/kg of 0.5% hydroxypropyl methylcellulose) and the rats are denied access to food and water for 6 more hours. The rats are then sacrificed with $CO_2$ so that the stomachs can be removed, opened along the greater curvature, and evaluated for the presence of gastric ulcers. Results are expressed as the percent of rats with gastric ulcers at a given dose or as the $UD_{50}$ (the dose which causes ulcers in 50% of the rats).

In addition to the compounds of formula I, the pharmaceutical compositions can also contain other active ingredients, such as cyclooxygenase inhibitors, nonsteroidal antiinflammatory drugs (NSAIDs), peripheral analgesic agents such as zomepirac, diflunisal, and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprofen aluminum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —$CH(CH_3)COOH$ or —$CH_2CH_2COOH$ group (which optionally can be in the form of a pharmaceutically acceptable salt group, e.g., —$CH(CH_3)COO^-NA^+$ or —$CH_2CH_2COO^-Na^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflanunatory drugs having a free —$CH_2COOH$ group (which optionally can be in the form of a pharmaceutically acceptable salt group, e.g. —$CH_2COO^-Na^+$), typically attached directly to a ring system, preferably to an aromatic or heteroaromatic ring system.

The fenamic acid derivatives which may be used comprise: mefenamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

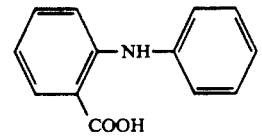

which can bear a variety of substituents and in which the free —COOH group can be in the form of a pharmaceutically acceptable salt group, e.g., —$COO^-Na^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

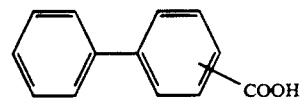

which can bear a variety of substituents and in which the free —COOH group can be in the form of a pharmaceutically acceptable salt group, e.g., —$COO^-Na^+$.

The oxicams which can be used in the present invention comprise: piroxicam, sudoxicam, isoxicam, and 4-hydroxyl-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

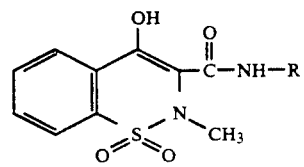

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, difisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I may also be advantageously combined with an H$_1$ or H$_2$-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a K$^+$/H$^+$ ATPase inhibitor such as omeprazole, disclosed in U.S. Pat. No. 4,255,431, and the like. Each of the references referred to in this paragraph is hereby incorporated herein by reference.

The compounds of the formula I and their salts are prepared generally by the following processes and constitute a further aspect of the present invention.

The compounds are prepared by the following schemes.

Compounds of formula I where n=1 and m=0-5 may be prepared as shown in Scheme 1 by acylation of the aminopyrimidine 1.

SCHEME 1

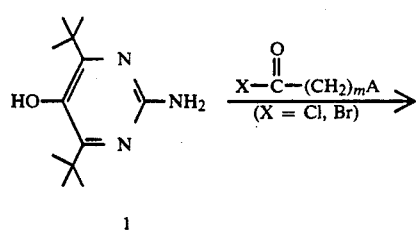

1

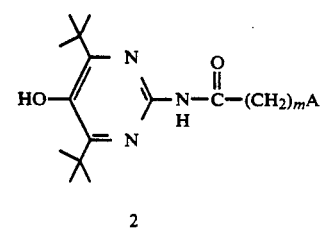

2

Compounds of formula I where n=0 and m=1-5 may be prepared as shown in Scheme 2 by acylation of aminopyrimidine 1 followed by reduction to the secondary amine 3.

SCHEME 2

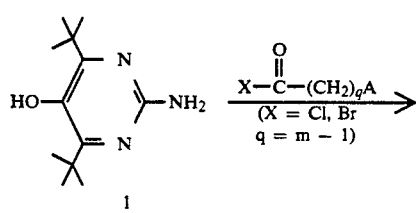

1

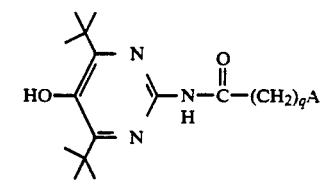

↓ DIBAL

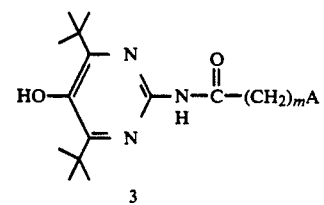

3

Compounds of the formula I where n=0 and m=0 may be prepared by the methods described in Scheme 3.

SCHEME 3
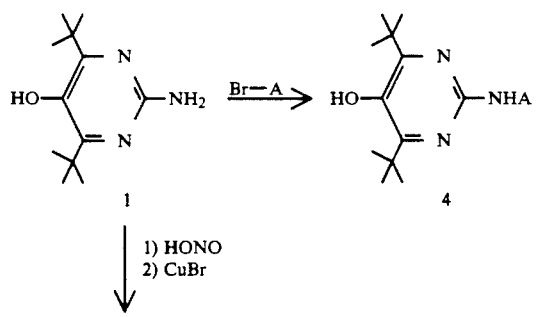
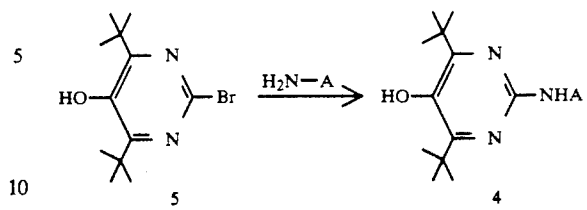
In some cases, the heteroaroatic ring, A, may be synthesized during the process of preparing compounds of formula I from pyrimidine 1 by known cyclization reactions. For example, thiazoles (8), imidazoles (9), and pyrimidines (10) may be prepared as shown in Scheme 4.
SCHEME 4
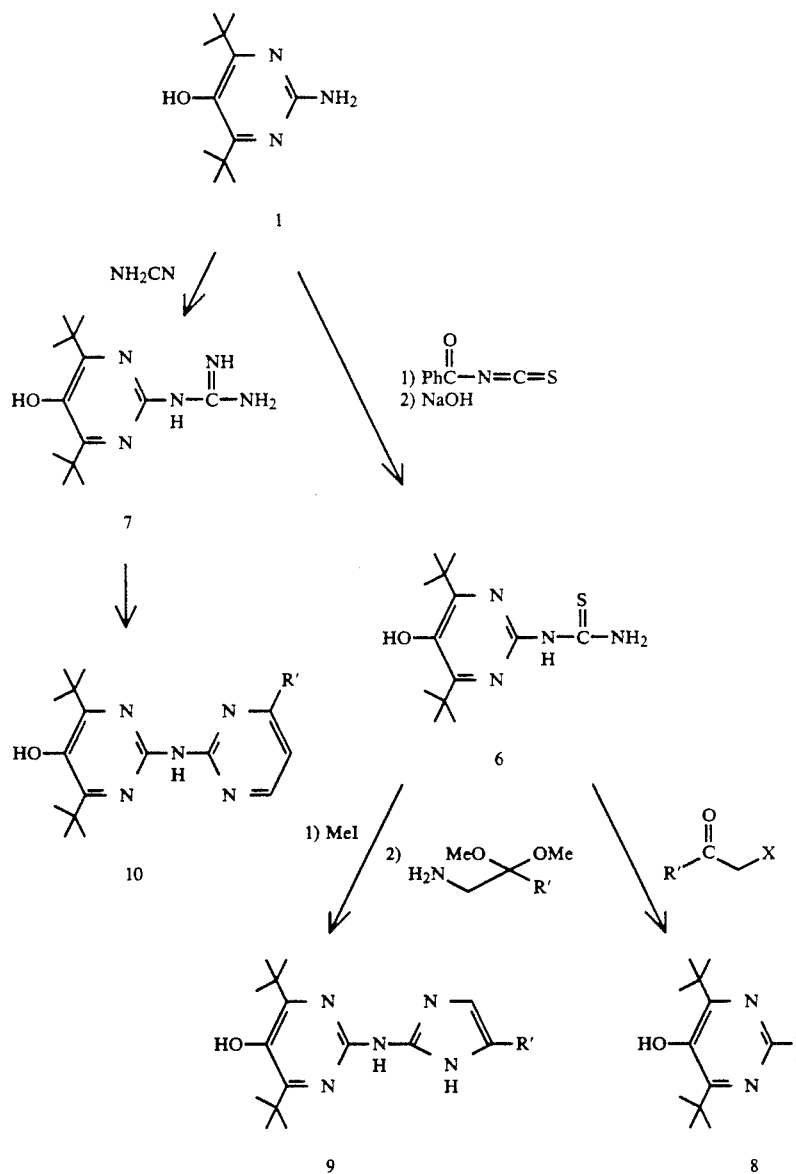
The starting aminopyrimidine 1 may be prepared as shown in Scheme 5.

SCHEME 5

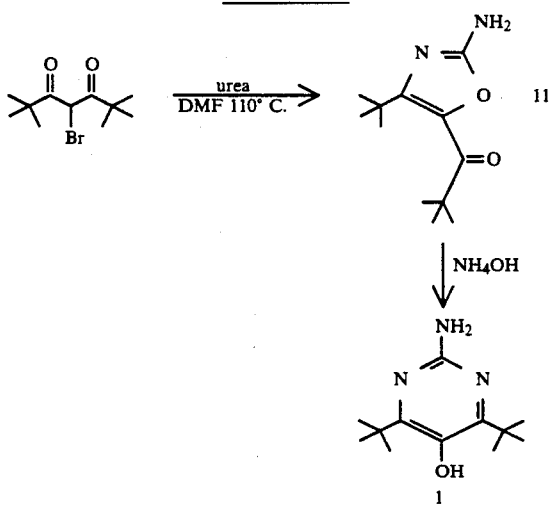

The reaction of the bromodiketone with urea, preferably in a solvent such as dimethylformamide (DMF), at a temperature of about 50° C. to reflux, preferably at 110° C., gives aminooxazole 11. Reaction of 11 with ammonium hydroxide at a temperature of about 130° C. to about 190° C., preferably at about 180° C., in a pressure reactor (closed vessel) and, preferably, in a solvent such as t-butanol gives aminopyrimidine 1.

The following working examples are illustrative in more detail of the preparation of the compounds of formula I.

EXAMPLE 1

1-[2-Amino-4-(1,1-dimethylethyl)-5-oxazolyl]-2,2-dimethyl-1-propanone

A mixture of 2,2,6,6-tetramethyl-4-bromo-3,5-heptanedione (70 g) and urea (77 g) in DMF (500 mL) is heated at 110°–120° C. overnight. The reaction mixture is cooled and poured into ice water (1500 mL) and the resulting precipitate is collected by filtration and air dried. The solid is rinsed with hexane (1000 mL) and then with isopropyl ether (200 mL) and dried under vacuum overnight to give 1-[2-amino-4-(1,1-dimethylethyl)-5-oxazolyl]-2,2-dimethyl-1-propanone (25.5 g, 42%); mp 248°–250° C.

EXAMPLE 2

2-Amino-4,6-bis(1,1-dimethylethyl)-5-hydroxy-pyrimidine

A solution of 1-[2-amino-4-(1,1-dimethylethyl)-5-oxazolyl]-2,2-dimethyl-1-propanone (15 g) in t-butanol (80 mL) and concentrated ammonium hydroxide (80 mL) is heated at 180° C. for 60 hours in a steel bomb. The reaction mixture is cooled and concentrated to half its volume on the rotovap. The product is extracted into ether (3×250 mL). The ether extract is dried (MgSO4) and evaporated. The residue is purified by flash chromatography (silica, 20% EtOAc/hexane) to give pure 2-amino-4,6-bis(1,1-dimethylethyl)-5-hydroxypyrimidine (4.5 g, 34%) which crystallizes from cold hexane; mp 92°–93° C.

EXAMPLE 3

4,6-Bis(1,1-dimethylethyl)-5-hydroxy-2-(3-pyridylamido) pyrimidine

A solution of 2-amino-4,6-bis(1,1-dimethylethyl)-5-hydroxypyrimidine (500 mg, 2.25 mmol) and nicotinoyl chloride hydrochloride (520 mg, 2.9 mmol) in pyridine is stirred at room temperature overnight. The solvent is evaporated and the residue is partitioned between ethyl acetate and dilute aqueous sodium bicarbonate. The organic layer is dried over MgSO4 and evaporated. Recrystallization of the residue from isopropyl ether gives pure 4,6-bis(1,1-dimethylethyl)-5-hydroxy-2-(3-pyridylamido)pyrimidine (180 mg, 25%); mp 165°–166° C.

EXAMPLE 4

N-[4,6-bis(1,1-dimethylethyl)-5-hydroxy-2-pyrimidinyl]thiourea

Benzoyl chloride (3.1 g, 22.4 mmol) is added dropwise to an acetone (25 mL) solution of ammonium thiocyanate (1.9 g, 24.6 mmol), and the resulting mixture is heated to reflux for 5 minutes. The heat is removed, and when refluxing stops, 4,6-bis(1,1-dimethylethyl)-5-hydroxy-2-aminopyrimidine (5.0 g, 22.4 mmol) is added to the hot reaction mixture as a solution in acetone (20 mL). After 10 minutes, the acetone is evaporated. The residue is taken up in ethyl acetate, and absorbed onto a silica gel pad. The pad is washed with 200 mL of 5% ether/hexane followed by 400 mL of ether. Evaporation of the ether gives 9 g of the intermediate benzoyl thiourea which is immediately dissolved in 40 mL of methanol. Forty milliliters of 1.0N KOH (aq) is added to this solution, and the reaction mixture is stirred at room temperature overnight. The methanol is removed under reduced pressure, and the aqueous solution remaining is neutralized with concentrated HCl to pH 7. The precipitate which forms is collected and air dried. It is then treated with boiling hexane for 10 minutes and collected by filtration. Yield of N-[4,6-bis(1,1-dimethylethyl)-5-hydroxy-2-pyrimidinyl]thiourea is 4.7 g (68%). An aliquot is recrystallized from ethyl acetate/isopropyl ether; mp 201°–203° C.

EXAMPLE 5

4,6-Bis(1,1-dimethylethyl)-21(4-methyl-2-thiazolyl)amino]-5-pyrimidinol

Chloroacetone (0.17 g, 1.9 mmol) is added to a solution of N-[4,6-bis(1,1-dimethylethyl)-5-hydroxy-2-pyrimidinyl]thiourea in 25 mL of ethanol. The reaction mixture is warmed to reflux for 18 hours. The solution is poured into 100 mL of water and the pH is adjusted to 4 with saturated NaHCO3. The resulting precipitate is collected by filtration. Recrystallization from hexane gives 0.26 g (45%) of 4,6-bis(1,1-dimethylethyl)-2-[(4-methyl-2-thiazolyl)amino]-5-pyrimidinol; mp 171°–173° C.

EXAMPLE 6

2-([4,6-Bis(1,1-dimethylethyl)-5-hydroxy-2-pyrimidinyl]amino)-4-thiazolecarboxylic acid ethyl ester N-[4,6-bis(1,1-dimethylethyl)-5-hydroxy-2-pyrimidinyl]thiourea (1.0 g, 3.5 mmol) is added to a solution of ethylbromopyruvate (0.72 g, 3.7 mmol) in 25 mL of ethanol. The mixture is warmed to reflux for 4.5 hours, then diluted with 100 mL of water. The pH of the solution is adjusted to 4 with saturated NaCHO₃. The resulting precipitate is collected by filtration and recrystallized from ethanol/water. Yield of 2-([4,6-bis(1,1-dimethylethyl)-5-hydroxy-2-pyrimidinyl-]amino)-4-thiazolecarboxylic acid ethyl ester is 0.86 g (65%). An analytical sample was obtained by treating an aliquot with boiling hexane for 10 minutes; mp 204°–206° C.

EXAMPLE 7

2-[[4,6-Bis(1,1-dimethylethyl)-5-hydroxy-2-pyrimidinyl]amino]-4-thiazolecarboxylic acid A solution of 2-([4,6-bis(1,1-dimethylethyl)-5-hydroxy-2-pyrimidinyl]amino)-4-thiazolecarboxylic acid ethyl ester (0.5 g, 1.3 mmol) in 20 mL of methanol is treated with 10 mL of 1.0N KOH (aq) at room temperature. After 3.5 hours, the methanol is removed under reduced pressure, and the aqueous solution is acidified to pH 4 with concentrated HCl. The resulting precipitate is collected by filtration and recrystallized from MeOH/water. Yield of 2-([4,6-bis(1,1-dimethylethyl)-5-hydroxy-2-pyrimidinyl]amino)-4-thiazolecarboxylic acid is 0.09 g (26%); mp 251°–253° C.

EXAMPLE 8

N-[4,6-Bis(1,1-dimethylethyl)-5-hydroxy-2-pyrimidinyl]-S-methyl isothiourea

Methyl iodide (1.05 g, 7.4 mmol) is added to an ethanol (50 mL) solution of N-[4,6-bis(1,1-dimethylethyl)-5-hydroxy-2-pyrimidinyl]thiourea (2.0 g, 7.1 mmol) and the mixture is heated at reflux under argon for 2.5 hours. The ethanol is evaporated under reduced pressure and the residue is taken up in 50 mL EtOAc. The EtOAc solution is washed with saturated NaHCO₃ (3×50 mL) and 50 mL of brine. Drying over MgSO₄ and evaporation of solvent gives an off-white solid. Recrystallization from ether/hexane gives 1.5 g (71%) of N-[4,6-bis(1,1-dimethylethyl)-5-hydroxy-2-pyrimidinyl]-S-methyl isothiourea; mp 163°–165° C.

EXAMPLE 9

N-[(4,6-Bis(1,1-dimethylethyl)-5-hydroxy-2-pyrimidinyl]-N'-(α-acetaldehyde diethyl acetal)quanidine A solution of 2-amino acetaldehyde diethyl acetal (1.25 g, 9.5 mmol) and N-[4,6-bis(1,1-dimethylethyl)-5-hydroxy-2-pyrimidinyl]-S-methyl isothiourea (0.5 g, 1.7 mmol) in 20 mL of 1:1 dioxane/water is heated, at 90° C. for 2 hours. The reaction mixture is diluted with 100 mL of water and cooled to room temperature. The resulting precipitate is collected by filtration and recrystallized from MeOH/water. Yield of N-[(4,6-bis(1,1-dimethylethyl)-5-hydroxy-2-pyrimidinyl]-N'-(α-acetaldehyde diethyl acetal)-guanidine is 0.16 g (25%); mp 242°–243° C. dec.

EXAMPLE 10

4,6-Bis(1,1-dimethylethyl)-2-[(2-imidazolyl)amino]-5-pyrimidinol

N-(4,6-Bis(1,1-dimethylethyl)-5-hydroxy-2-pyrimidinyl-S-methyl isothiourea (1.5 g, 5.1 mmol) is added to a solution of aminoacetaldehyde diethyl acetal (3.4 g, 25.3 mmol) in 40 mL of 1:1 dioxane/water. The resulting mixture is warmed to 90° C. for 3 hours. The solvent is removed under reduced pressure and the remaining solid is treated with 6 mL of concentrated HCl. The reaction mixture is warmed on the steam bath for 15 minutes, at which time 10 mL of water is added. The mixture is evaporated to dryness on the steam bath. This addition/evaporation of water is repeated two more times. The solid remaining is partitioned between 20 mL of water and 50 mL of ethyl acetate. The organic layer is washed with 50 mL of brine and dried over MgSO₄. Evaporation of solvent followed by recrystallization from isopropyl ether/ethyl acetate gives 0.18 g (12%) of 4,6-bis(1,1-dimethylethyl)-2[(2-imidazolyl)amino]-5-pyrimidinol; mp 235°–238° C. dec.

Analysis for C₁₅H₂₃N₅O:
Calcd: C, 62.26; H, 8.01; N, 24.20; Found: C, 61.98; H, 8.06; N, 24.45.

We claim:

1. A method of using an aminooxazole of the formula

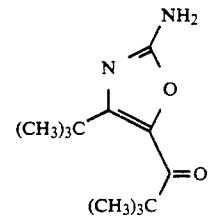

to prepare a compound of the formula 1

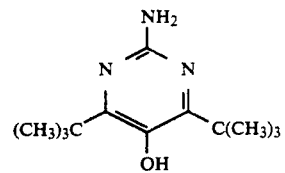

by reacting the aminooxazole with ammonium hydroxide at about 130° C. to about 190° C. in a closed vessel.

* * * * *